US 6,913,692 B2

(12) United States Patent
Margraff et al.

(10) Patent No.: US 6,913,692 B2
(45) Date of Patent: Jul. 5, 2005

(54) ROTATING DEVICE FOR CENTRIFUGAL PARTITION CHROMATOGRAPH

(75) Inventors: Rodolphe Margraff, Villenauxe-la-Petite (FR); Pierre Garret, Banvillars (FR); Jean-Hugues Renault, Reims (FR)

(73) Assignee: Partus Technologies, Reims (FR)

( * ) Notice: Subject to any disclaimer, the term of this patent is extended or adjusted under 35 U.S.C. 154(b) by 75 days.

(21) Appl. No.: 10/600,811

(22) Filed: Jun. 20, 2003

(65) Prior Publication Data

US 2004/0173534 A1 Sep. 9, 2004

(30) Foreign Application Priority Data

Mar. 8, 2003 (FR) .............................. 03 02769

(51) Int. Cl.[7] .............................................. B01D 15/08
(52) U.S. Cl. ..................... 210/198.2; 210/635; 210/657
(58) Field of Search ................................ 210/635, 656, 210/657, 198.2

(56) References Cited

U.S. PATENT DOCUMENTS

| 3,775,309 A | * | 11/1973 | Ito ............................. 210/635 |
| 4,051,025 A | * | 9/1977 | Ito ............................. 210/635 |
| 4,551,251 A | * | 11/1985 | Kolobow et al. ........... 210/635 |
| 4,857,187 A | | 8/1989 | Ito ........................ 210/198.2 |
| 4,968,428 A | | 11/1990 | Nunogaki ................... 210/635 |
| 6,537,452 B1 | * | 3/2003 | de La Poype et al. ... 210/198.2 |

FOREIGN PATENT DOCUMENTS

FR 2791578 10/2000

OTHER PUBLICATIONS

"Centrifugal Partition Chromatography (CPC): Emerging Separation And Purification Technique For Lipid And Related Compounds", Wanasundara et al., INFORM, vol. 13, No. 9, 2002, pp. 726–730.

* cited by examiner

Primary Examiner—Ernest G. Therkorn
(74) Attorney, Agent, or Firm—Perman & Green, LLP

(57) ABSTRACT

The rotating device for a centrifugal partition chromatograph comprises at least one thick-walled cylindrical body (1) that can be driven in rotation around its axis (14), the said cylindrical body (1) comprising several cells with a height less than a determined height. The cells, arranged in the housings (11), have an elongated shape arranged along a direction with a radial component with regard to the rotation axis (14) of the said body (1) and connected to each other in series through ducts. The single piece cylindrical body (1) has a thick wall, with a height (H) at least twice as high as the said determined height, the said cells being arranged at several different heights.

For example, several hundred cells may be arranged in the single piece cylindrical body (1). The rotating device resists pressures well above 100 bars and can be used for industrial applications.

18 Claims, 3 Drawing Sheets

ROTATING DEVICE FOR CENTRIFUGAL PARTITION CHROMATOGRAPH

This invention relates to equipment for separation of liquids by counter current circulation of liquids. The invention is more particularly applicable to a rotating device for centrifugal partition chromatographs.

The centrifugal partition chromatography (CPC) is a method of liquid-liquid separation derived from the definition given above. The CPC method is adapted to separate compounds of a mix between a mobile phase and a stationary phase, the affinities of the compounds to be separated being different for the two phases.

The two liquid phases are immiscible. In CPC equipment, the separation is done in a circuit formed by ducts connecting the so-called separation cells in series. The stationary phase is kept in the circuit due to a centrifugal force field while the other mobile phase circulates through the stationary phase.

Flow of the mobile phase through the stationary phase is a very important factor for obtaining good separation. This flow may be improved using a configuration optimized for a chromatography circuit.

U.S. Pat. No. 4,968,428 describes a counter-current chromatography device using stacked flat disks driven in rotation. These disks comprise several cells connected to each other in series through thin channels perforated or etched on the said disks. The stacked disks are interconnected through pipes.

Patent FR 2 791 578 uses the same stacked rings device to form a cylindrical rotor modifying the connections between the cells and the ducts, that from radial in the US patent become axial, by inclining the cells with respect to the radii of the rings in order to improve the efficiency of the device that is based on dispersion of the mobile phase jet entering into the cell containing the stationary phase.

In the two inventions mentioned above, the disks are separated by Teflon® sheets to close the cells and assure leak tightness of the rotor consisting of an alternating stack of alternated disks and Teflon® sheets forming the joint. The assembly is held in place by bolting. These devices are limited to pressures (BACK PRESSURE) less than about 60 bars, imposed by the limiting pressure applicable to the mechanical assembly device by bolts to prevent excessive creep of the Teflon@. These devices are useful for analytic applications, but are not suitable for industrial use.

Therefore, the purpose of this invention is to overcome one or several of the disadvantages according to prior art by proposing a robust rotating device for CPC chromatographs in order to push back well this pressure limitation beyond the hundred bars and that can be used in industrial production.

This purpose is achieved by a rotating device for a centrifugal partition chromatograph, comprising at least one cylindrical body that can be driven in rotation around its axis, the said cylindrical body comprising several cells, with a height less than a determined height, with an elongated shape arranged along a direction with a radial component with regard to the rotation axis of the said body, the cells being connected to each other in series through ducts internal to the body and external, characterized in that the said cylindrical body has a thick single piece wall, at least twice a high as the said determined height, the said cells being arranged at several different heights in the body, the internal ducts in the body being arranged along a direction with a radial component.

According to another feature, the cells arranged side by side in the body and connected in series to each other by inlet and outlet ducts opening up at the ends opposite the said cells, are distributed along a helical spiral around the rotation axis of the body.

According to another feature, the cells arranged side by side in the said body and connected to each other in series by inlet and outlet ducts opening up at the ends opposite the said cells, are distributed by successive planes orthogonal to the rotation axis of the body.

According to another feature, the cylindrical body comprises several open cavities on the side of the outer wall of the said body, each cavity opening up on one face of the body through an enlarged opening to insert an associated internal duct, first removable closing means covering the said opening and forming a communication channel with a perforating partition between the cavity and the associated internal duct.

According to another feature, the cylindrical body comprises several open cavities on the inside and outside of the body (1), the cavities being closed by closing means comprising cylindrical parts in which communication channels are hollowed out to connect a cavity to an associated internal duct, the said closing means being assembled on each side of the cylindrical body by strapping.

According to another feature, the cylindrical body comprises several open cavities on the side of the outer wall of the said body, each cavity comprising several housings to insert several cells with their associated internal ducts, first removable closing means covering the cells and the internal ducts in the same cavity.

According to another feature, the said first closing means comprise a plug, a sealed partition forming a sealing element on the body, and at least one plug attachment element on the body, the plug coming into contact with the sealing element.

According to another feature, the first closing means comprise a plug provided with a seal placed on a contact surface of the opening of the cavity, the plug comprising at least one recess to form a connecting channel between a cell and the associated internal duct.

According to another feature, the plug is held directly or indirectly by a screwing element.

According to another feature, the cavities also comprise an opening on the side of the inner wall of the cylindrical body, the cross section of the said opening being smaller than a median cross section of the cavity and communicating with a connecting channel between a cavity and an internal duct associated with the adjacent cavity, the channel being formed by a recess in the second closing means.

According to another feature, the second closing means are held in place on the inner wall by attachment means and are in contact with a seal.

According to another feature, the single piece cylindrical body comprising titanium and/or aluminium has an outside diameter of between 20 cm and 2 m and comprises at least 50 cell housings.

According to another feature, the cylindrical body comprises an alternating series of cells and ducts arranged in a synthetic resin block formed by moulding.

According to another feature, the said determined height is between 2 and 50 mm, the cells being identical to each other and having their largest dimension oriented along a radial direction.

According to another feature, the thickness of the cylindrical body between its inner wall and outer wall is between 25 and 500 mm, the largest dimension of the cells being between 0.2 and 0.95 times the said thickness of the body and oriented along a radial direction.

According to another feature, the body comprises an associated opening for each cell and a dispersion element for the cell lining.

According to another feature, the cells comprise a titanium or stainless steel or fluorinated polymer internal surface, the internal volume of the cells being between 5 and 200 cm$^3$.

According to another feature, an external metal pipe connects the cell to the internal ducts, the ends of the external pipe being fitted with Swagelock type connectors.

The invention also relates to use of the rotating device for a separation/purification operation of the constituents of a mix, these constituents being in particular organic molecules, metallic cations or plasmid DNA.

This objective is achieved by use of the rotating device according to the invention, characterized in that the said single piece approximately cylindrical body is driven in rotation about its axis during a separation/purification operation to isolate a compound from a mix, one or more fluids possibly being brought into the supercritical state inside a circuit in the rotating device.

The invention with its characteristics and advantages will become more easily understandable after reading the following description with reference to the attached drawings in which:

DESCRIPTION OF THE PREFERRED EMBODIMENTS

Figure 1:
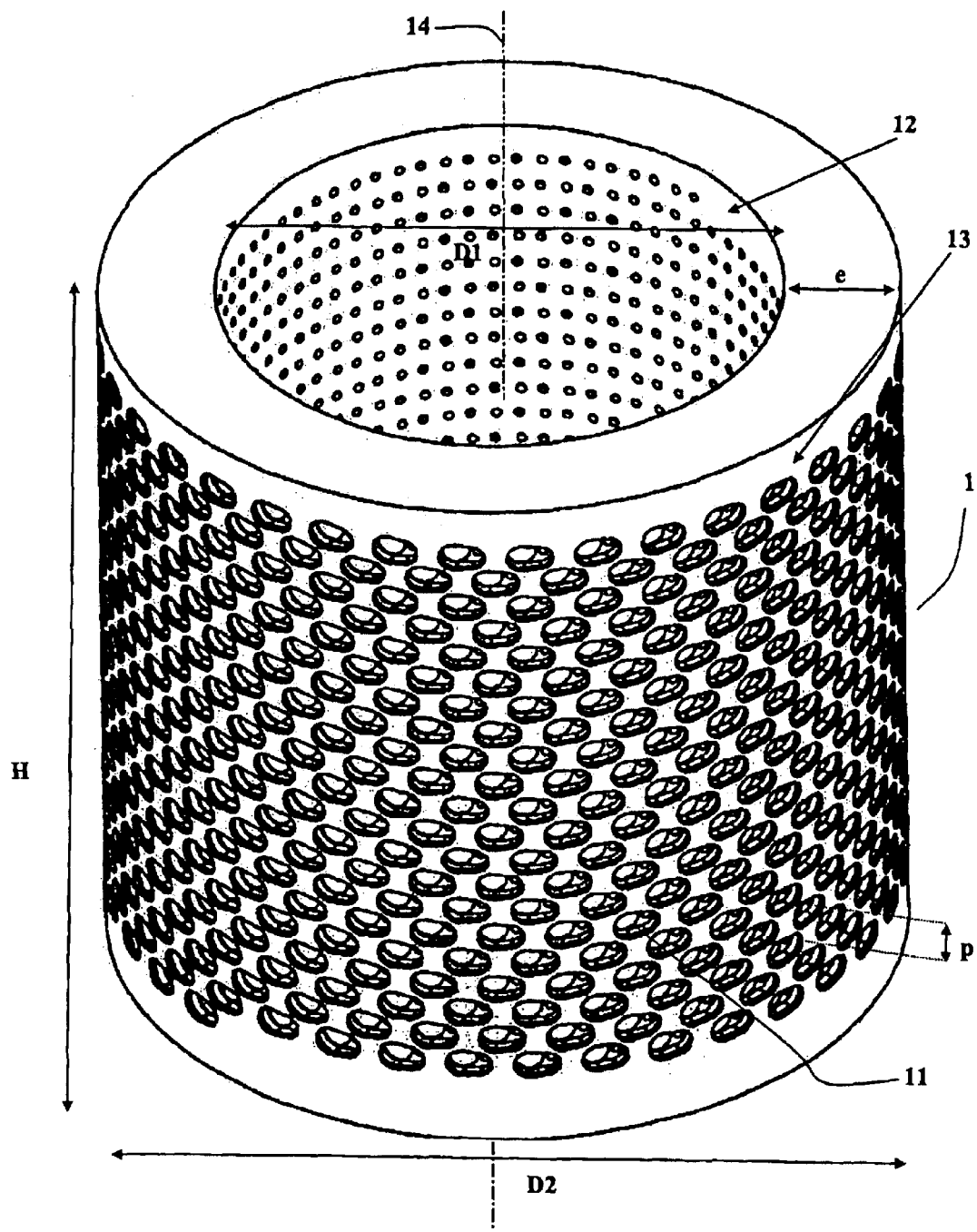
FIG. 1 shows a perspective view of an embodiment of the device according to the invention, with a helical distribution of the cells.
Figure 2:
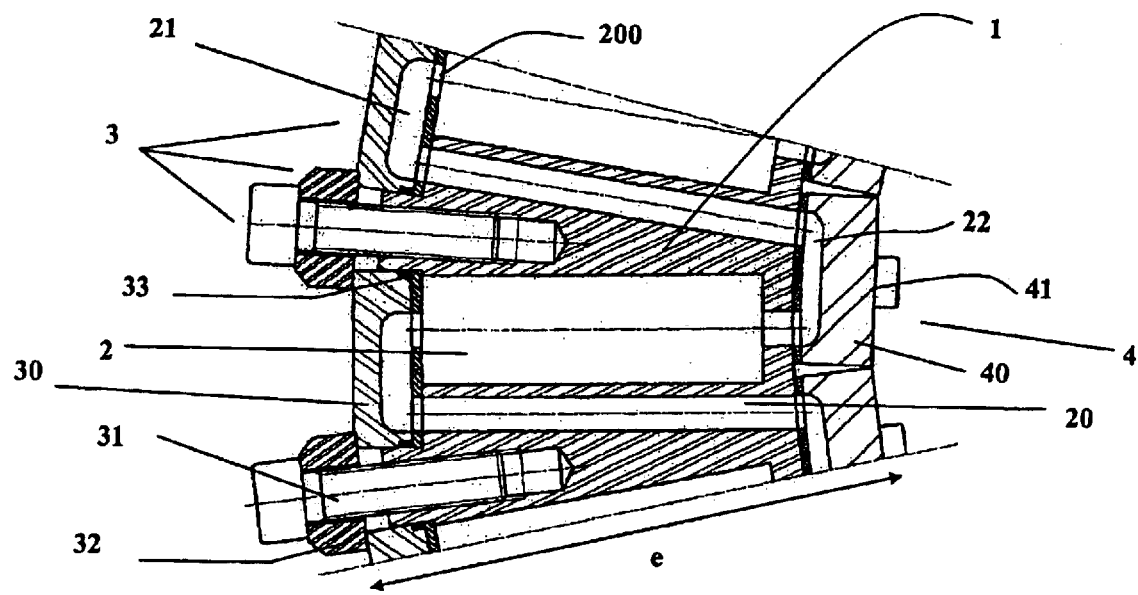
FIG. 2 shows a horizontal sectional view of the inside of the body of the cylindrical wall, according to an embodiment of the invention, FIG. 3 diagrammatically illustrates the layout of the circuit in series with alternation of cells and ducts in one embodiment with a helical distribution of the cells, FIG. 4 diagrammatically illustrates an example of a connection of the circuit that can be used in an embodiment with a symmetrical distribution of cells about the rotation axis.
Figure 3:
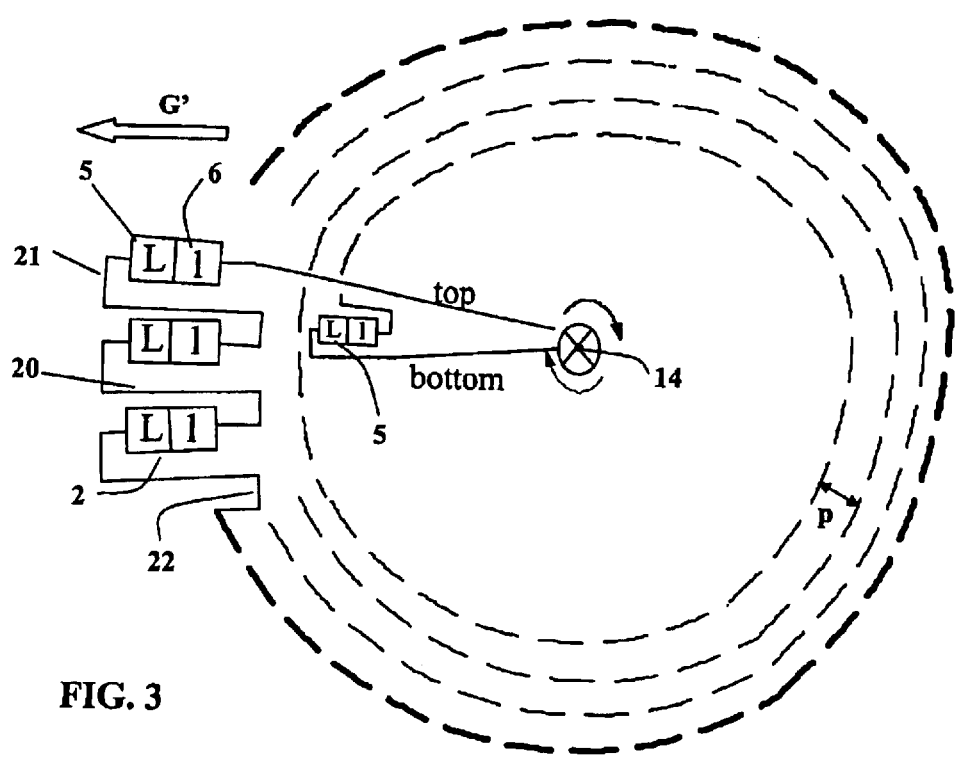

We will now describe the invention with reference to FIGS. 1, 2 and 3. For example, the single piece cylindrical body (1) with a thick wall in the rotating device is made of titanium, 316 L stainless steel or aluminium with a titanium or PVDF (vinylidene polyfluoride) lining. The material used may also be a composite, possibly with a titanium or PVDF lining. The cylindrical body (1) may consist simply of a synthetic resin block formed by moulding. In this case, an alternating series of cells and ducts was previously deposited in a double cylindrical mould before pouring a synthetic resin block. The thickness of the cylindrical body (1) between its inner wall (12) and its outer wall (13) may for example be between 25 and 500 mm.

The cylindrical body (1) comprises an inner wall (12) and an outer wall (13) and may be driven in rotation about its axis (14) arranged vertically or horizontally. The device according to the invention may thus be used as a rotor in a centrifugal partition chromatograph, a rotation drive shaft that for example can be inserted in the empty space delimited by the inner wall (12) of the cylindrical body (1). The drive means of the rotating device, of a known type, are not shown. The inside diameter (D1) of the cylindrical body (1) is larger than a few centimetres, particularly to enable a rotating shaft to pass through, and may for example be less than 60 cm. The outside diameter (D2) is at least 4 centimetres more than the inside diameter, and may for example be between 20 and 200 cm.

As shown on FIG. 1, the rotating device according to the invention comprises several housings (11) formed in the cylindrical body (1) and that in particular will contain cells (2). These cells (2), usually called separation cells, are distributed in the thick wall of the cylindrical body (1) all around its rotation axis (14). These cells (2) have an elongated shape and are arranged along a direction with a radial component with respect to the rotation axis (14) of the said body (1). As illustrated in FIG. 2, the cells (2) are made in series with each other connected by ducts (20) internal to the body, and external ducts (21, 22). As a variant, these ducts (20, 21, 22) may all be internal. In one embodiment of the invention, the dimensions of all cells (2) are the same and their height is less than a determined height, for example between 2 and 50 mm. The height of the single piece cylindrical body (1) (H) is equal to at least twice this determined height and the cells (2) are arranged at several height levels in the body (1). Thus, the rotating device is particularly compact and may comprise a large number of cells, for example at least 50 cells. For example, in the embodiment shown in FIG. 1, the body comprises 766 housings (11) each of which will accommodate one cell (2).

The cells (2) are arranged side by side in the body (1) and are connected to each other in series by inlet and outlet ducts (20, 21, 22) opening up at the opposite ends of the said cells (2). In a first embodiment of the invention, the cells (2) are arranged in a spiral helix around the rotation axis (14) of the body (1), for example over most of the height (H) of the cylindrical body. As shown on FIG. 3, the cells (2) are placed radially with regard to the rotation axis (14) of the body (1) and for example form a circular helix with a constant pitch (p). The largest dimension of the cells, or the length, arranged along the radial direction, is between 0.2 and 0.95 times the thickness (e) of the body (1). The connection between two consecutive cells is made particularly using an internal duct (20) inside the body (1) and two external ducts forming channels (21, 22) connecting the cells (2) at their opposite ends. The inner ducts (20) are arranged along a direction with a radial component with respect to the rotation axis (14) of the cylindrical body (1).

In the rotating device, the end connections are made with two rotating seals on each side of the rotor formed by the cylindrical body (1). Connections with the first and the last separation cells are designed such that the mobile face circulates in the separation cells (2) during the partition operation:

in the direction of the force field, in other words from the inside towards the outside of the cylindrical body (1) if it corresponds to the heavy phase (5);

in the opposite direction if it corresponds to the light phase (6).

In the special case in which the rotor is arranged vertically, these connections are designed so that when the heavy phase (5) forms the mobile phase, the flow direction in the circuit goes from the top of the rotor towards the bottom of the rotor and vice versa when the light phase (6) is the mobile phase.

The centrifugal force field (G') created during rotation of the device can easily be equal to 100 or more times the acceleration due to gravity. In one embodiment of the invention, rotation of the rotating device takes place at speeds of between 100 and 1500 rev/min, for example 600 rev/min. The robustness of the cylindrical body (1) and the large number of cells (2) integrated into this body enable industrial use of the rotating device according to the invention. Relatively high production rates can be envisaged with this device, and the maximum supported pressure can reach or even exceed 150 bars. The ends of the circuit performing inlet and outlet functions may for example be connected to a connector with a rotating seal screwed onto a shaft coincident with the rotation axis (14) of the cylindrical body. A tube can connect each of the ends to a rotating seal. In one embodiment of the invention, the rotating device can resist a pressure of about 250 bars.

FIG. 2 shows an example of an arrangement used for each of the cells (2) in one embodiment of the invention. The cylindrical body (1) comprises several cavities within its thickness (e) open on the side of the outer wall (13) of the said body. Each cavity comprises a housing (11) to insert a cell (2) and opens up onto an outside face of the block through an enlarged opening to insert an associated internal duct (20). In the embodiment shown in FIG. 2, the first removable closing means (3) cover the said enlarged opening. For example, the material forming or covering cells and ducts (20, 21, 22) is made of titanium. Stainless steel or a fluorinated polymer may also be used instead of titanium. The same type of material is used for exit connectors from the circuit.

In the embodiment shown in FIG. 2, the first closing means (3) comprise a plug (30) provided with a seal (33) and comprise at least one recess to form a connecting channel (21) between a cell (2) and the associated inside duct (20). At least one screwing element (31) is used to fix the plug (30). As a variant, these first closing means (3) may consist of an external plug (30) and a sealed partition forming a seal on the body (1). In one embodiment of the invention, the plug (30) is held directly or indirectly in place by the said screwing element (31) and is in contact with the seal (33) placed on a bearing surface of the opening of the cavity. For example, two screws can block the plug (30) that covers a cell (2) and the associated internal duct (20) at the same time. The cylindrical body (1) comprises two threaded female parts placed at two opposite ends of the opening of the cavities to contain the said screws. An intermediate part (32) is placed between the head of each screw and the end of the plug (30) adjacent to a threaded female part. A sharpened lock may be provided to prevent the risk of screwing elements (31) coming loose under the effect of the centrifugal force. In the variant embodiment shown in FIG. 2, the plug (30) comprises at least one sealed and drilled partition to form a connecting channel between the cavity corresponding to a cell (2) and an associated internal duct (20).

In different embodiments, the cavities open on the side of the outer wall incorporate several housings in which several cells (2) with associated ducts can be inserted. Removable closing means (not shown) can be used to cover the cells (2) and ducts in the same cavity. These closing means may comprise screwing elements similar to the first closing means (3). For example, the cover plug may cover several drillings to form connecting ducts that are positioned facing the cells (2) and internal ducts (20) associated in pairs.

In one embodiment of the invention, the cavities also comprise an opening on the side of the inside wall (12) of the cylindrical body (1). This opening is closed off by second closing means (4) comprising at least one cover part (40) with a recess to form a connecting channel (22) between a cavity containing a cell (2) and an internal duct (20) associated with the adjacent cavity. The said first and second closing means may for example be metallic, the plugs (30) and the cover parts (40) possibly including a titanium or stainless steel coating on their recessed area. These second closing means (4) may for example be used for all cavities, except for cavities corresponding to the circuit inlet and outlet ends. The cover part (40) is removable. It comprises an extension (41) that may be manoeuvred to withdraw the cover part (40) by loosening it. The closing means (3, 4) may also comprise cylindrical parts in which communication channels are hollowed out to connect a cavity to an associated internal duct (20). In one embodiment of the invention, these closing means (3,4) are assembled on each side of the cylindrical body (1) by strapping.

In one embodiment of the invention, an external metallic pipe connects the cells (2) to the internal ducts (21). The ends of the external pipe may advantageously be equipped with Swagelock type connectors to keep the circuit leak tight.

The invention will now be described with reference to FIGS. 4, 5A, 5B, 5C and 6.

Figure 4:
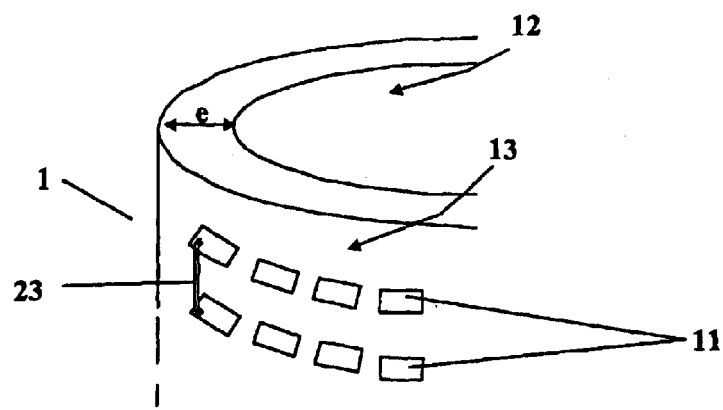

In the embodiment shown in FIG. 4, the cells (2) are arranged in the housings (11) placed side by side in the single piece cylindrical body (1) distributed in successive planes orthogonal to the rotation axis (14) of the body (1). In this embodiment, the number of cells (2) may also be equal to at least 700. Thus, the cylindrical body (1) comprises several "layers" of cells (2) each grouped at the same height level, and "inter-layer" connecting ducts (23), external to the body (1) are provided to connect two adjacent "layers". These connecting ducts (23) may for example be placed around the periphery of the outer wall (13) as shown on FIG. 4, or placed on the inner wall (12). Naturally, the cavities connected to these connecting ducts (23) may comprise closing means with sealing elements different from the closing means (3,4) used for the other cavities.

Figures 5A, 5B, 5C:
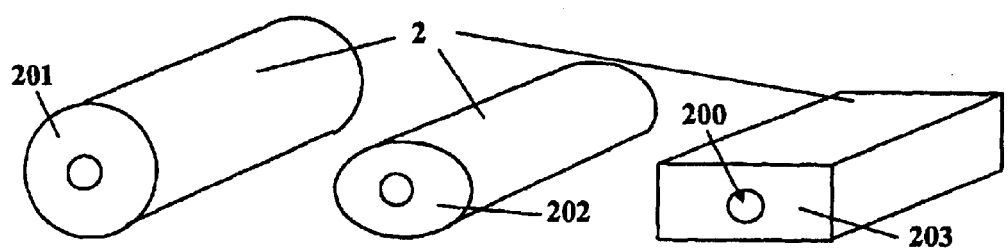
FIGS. 5A, 5B and 5C show different variant embodiments of cells that can be used in the invention.

According to one feature of the invention, the section of the cells (2) is regular and their internal volume is between 5 and 200 cm³. The section of the cells (2) may be circular (201), oblong (202) or rectangular (203) as illustrated in FIGS. 5A, 5B and 5C. The cylindrical body (1) comprises an associated opening for each of the cells (2) and a dispersion element for the cell lining. Thus, each cell (2) is removable and may easily be cleaned or replaced. Lining braids or any other porous dispersion element with a large surface-volume ratio may be inserted into the cells (2) through their opening located on the side of the outer wall (13). These braids (not shown) encourage dispersion of the mobile phase in the stationary phase, and for example occupy 3% of the volume of the cell. In one embodiment of the invention, the section of the ducts associated with the cells (2) may be circular, but other forms would be possible, for example rectangular, oblong, etc. The dimensions of this duct section correspond to the dimensions of the inlet or outlet hole (200) of the cells (2).

Figure 6:
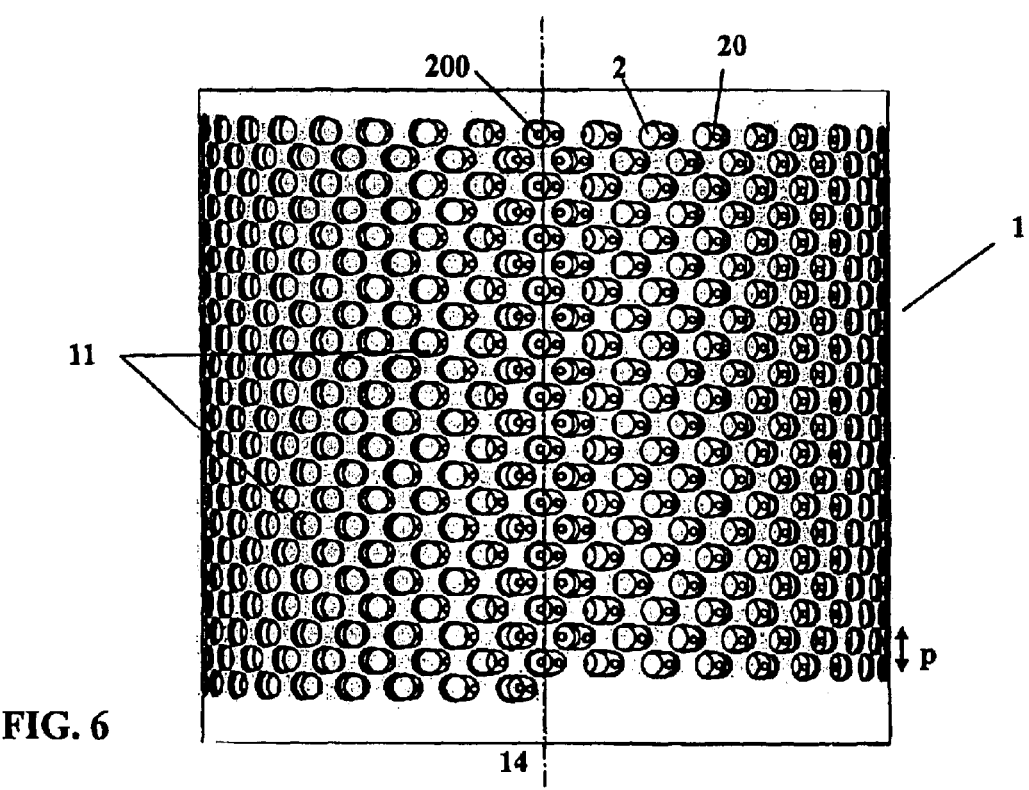
FIG. 6 shows a front view of an embodiment of the device according to the invention with a helical distribution of the cells.

FIG. 6 shows an example embodiment of the rotating device according to the invention, the outer openings not being covered by the first closing means (3). A cell (2) and an inner duct (20) are arranged in each housing (11). The layout of the housings (11) may be made more compact to minimize the height (H) of the cylindrical body (1) by offsetting housings (11) in pairs along a vertical direction as shown in FIG. 6. This offset in the vertical alignment of the housings (11) is a means of increasing the number of cells (2), while maintaining excellent robustness of the rotating device.

One example of an industrial application of the invention is use of the rotating device in a separation/purification operation in order to isolate a compound from a mix. The single piece cylindrical body (1) is then driven in rotation about its axis (14) while a liquid with at least two immiscible phases is added into the rotating device. It can be understood that the robustness of the rotating device according to the invention makes it possible to reliably and industrially make separations. The invention is suitable for the production of several hundred kilograms per year of high added value compounds. The use of titanium or aluminium in particular can reduce the weight of the rotating device to less than 500 kg, for example in one embodiment of the invention in which the outside diameter (D2) is less than 75 cm and the height (H) is less than 70 cm.

Cladding can be provided to make the rotating device safe. A protection system with a locked door may form the envelope of a centrifugal partition chromatograph in which the rotating device according to the invention is fitted.

One of the advantages of the device according to the invention is that capacities of up to for example 25 liters can be achieved to enable separation of much larger quantities than are possible with equipment now available on the market, for which capacities are limited to 5.4 liters.

Another advantage of the invention is the use of a single piece cylindrical body (1) for which no particular assembly is necessary, and cells accessible individually by disassembly of the closing means.

Another advantage of the rotating device is the possibility of operating at rotation speeds generating large centrifugal forces that can improve the chromatographic efficiency of some two-phase solvent systems. In one embodiment of the invention, the rotation speed can be as high as approximately 1500 rev/minute.

Another advantage resulting from the invention is the possibility of using fluids in the supercritical state, the withstood being able to reach 150 bars.

It must be obvious to persons skilled in the art that this invention can be used in many other specific forms without going outside the scope of the invention as claimed. Consequently, these embodiments must be considered as illustrations, but they may be modified within the range defined by the scope of the attached claims, and the invention must not be limited to the details described above.

What is claimed is:

1. Rotating device for a centrifugal partition chromatograph, comprising at least one cylindrical body that can be driven in rotation around its axis, the said cylindrical body comprising several cells with a height less than a determined height, with an elongated shape arranged along a direction with a radial component with regard to the rotation axis of the said body and being connected to each other in series through ducts internal to the body and external ducts, characterised in that the thick-walled single piece cylindrical body has a height at least twice as high as the said determined height, the said cells being arranged at several different heights in the body, the internal ducts in the body being arranged along a direction with a radial component.

2. Device according to claim 1, in which the cells, arranged side by side in the body and connected in series to each other by inlet and outlet ducts opening up at the ends opposite the said cells, are distributed in a helical spiral around the rotation axis of the body.

3. Device according to claim 1, in which the cells, arranged side by side in the said body and connected to each other in series by inlet and outlet ducts opening up at the ends opposite the said cells, are distributed by successive planes orthogonal to the rotation axis of the body.

4. Device according to claim 1, in which the cylindrical body comprises several open cavities on the side of the outer wall of the said body, each cavity opening up on one face of the body through an enlarged opening to insert an associated internal duct, first removable closing means covering the said opening and associated with a perforated partition to form a communication channel between the cavity and the associated internal duct.

5. Device according to claim 4, in which the said first closing means comprise a plug, a sealed partition forming a sealing element on the body, and at least one plug attachment element on the body, the plug coming into contact with the sealing element.

6. Device according to claim 5, in which the plug is held directly or indirectly by a screwing element.

7. Device according to claim 4, in which the first closing means comprise a plug provided with a seal placed on a contact surface of the opening of the cavity, the plug comprising at least one recess to form a connecting channel between a cell and the associated internal duct.

8. Device according to claim 4, in which the cavities also comprise an opening on the side of the inner wall of the cylindrical body, the cross section of the said opening being smaller than a median cross section of the cavity and communicating with a connecting channel between a cavity and an internal duct associated with the adjacent cavity, the said channel being formed by a recess in the second closing means.

9. Device according to claim 8, in which the second closing means are held in place on the inner wall by attachment means and are in contact with a seal.

10. Device according to claim 1, in which the cylindrical body comprises several open cavities on the inside and outside of the body, the cavities being closed by closing means comprising cylindrical parts in which communication channels are hollowed out to connect a cavity to an associated internal duct, the said closing means being assembled on each side of the cylindrical body by strapping.

11. Device according to claim 1, in which the cylindrical body comprises several open cavities on the side of the outer wall of the said body, each cavity comprising several housings to insert several cells with their associated internal ducts, first removable closing means covering the cells and the internal ducts in the same cavity.

12. Device according to claim 1, in which the single piece cylindrical body, comprising titanium and/or aluminum, has an outside diameter of between 20 cm and 2 m and comprises at least 50 housings of cells.

13. Device according to claim 1, in which the cylindrical body comprises an alternating series of cells and ducts arranged in a synthetic resin block formed by moulding.

14. Device according to claim 1, in which the said determined height is between 2 and 50 mm, the cells being identical to each other and having their largest dimension oriented along a radial direction.

15. Device according to claim 1, in which the thickness of the cylindrical body between its inner wall and outer wall is between 25 and 500 mm, the largest dimension of the cells being between 0.2 and 0.95 times the said thickness of the body and oriented along a radial direction.

16. Device according to claim 1, in which the body comprises an associated opening for each cell and a dispersion element for the cell lining.

17. Device according to claim 1, in which the cells comprise a titanium or stainless steel or fluorinated polymer internal surface, the internal volume of the cells being between 5 and 200 $cm^3$.

18. Device according to claim 1, in which an external metal pipe connects the cells to the internal ducts, the ends of the external pipe being fitted with Swagelock type connectors.

* * * * *